(12) United States Patent
Peters

(10) Patent No.: US 7,994,323 B2
(45) Date of Patent: Aug. 9, 2011

(54) CHROMEN-2-ONE DERIVATIVES

(75) Inventor: Dan Peters, Malmö (SE)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/599,186

(22) PCT Filed: May 8, 2008

(86) PCT No.: PCT/EP2008/055683
§ 371 (c)(1),
(2), (4) Date: Feb. 9, 2010

(87) PCT Pub. No.: WO2008/138854
PCT Pub. Date: Nov. 20, 2008

(65) Prior Publication Data
US 2010/0217002 A1   Aug. 26, 2010

Related U.S. Application Data

(60) Provisional application No. 60/917,183, filed on May 10, 2007.

(30) Foreign Application Priority Data

May 9, 2007   (DK) .................................. 2007 00692

(51) Int. Cl.
*C07D 451/06* (2006.01)
(52) U.S. Cl. ........................................................ 546/126
(58) Field of Classification Search .................. 546/126
See application file for complete search history.

(56) References Cited

U.S. PATENT DOCUMENTS 6,034,121 A   3/2000   O'Mahony et al.

FOREIGN PATENT DOCUMENTS

| EP | 1 130 020 | 9/2001 |
|---|---|---|
| WO | WO 02/102801 | 12/2002 |
| WO | WO 03/106452 | 12/2003 |
| WO | WO 2004/113334 | 12/2004 |
| WO | WO 2005/026143 | 3/2005 |
| WO | WO 2006/035034 | 4/2006 |
| WO | WO 2006/064031 | 6/2006 |
| WO | WO 2008/074797 | 6/2008 |
| WO | WO 2008/074798 | 6/2008 |

OTHER PUBLICATIONS

Maksay et al., Journal of medicinal Chemistry (2004), 47(25), pp. 6384-6391.*
Jackson et al., "Design, Synthesis and Characterization of a Novel Class of Coumarin-Based Inhibitors of Inducible Nitric Oxide Synthase", Bioorganic & Medicinal Chemistry, vol. 13 (2005) pp. 2723-2739.
Wallace et al., "New Compounds: Synthesis of para-Substituted Nortropanyl Benzoates", Journal of Pharmaceutical Sciences, vol. 69, No. 11 (1980) pp. 1357-1358. XP-002491173.

* cited by examiner

*Primary Examiner* — D Seaman
*Assistant Examiner* — Niloofar Rahmani
(74) *Attorney, Agent, or Firm* — Birch, Stewart, Kolasch & Birch, LLP.

(57) ABSTRACT

This invention relates to novel chromen-2-one derivatives useful as starting material for synthesis of pharmaceuticals. On other aspects the invention relates to a method of preparing the chromen-2-one derivatives of the invention.

15 Claims, No Drawings

CHROMEN-2-ONE DERIVATIVES

This application is the National Phase of PCT/EP2008/055683 filed on May 8, 2008, which claims priority under 35 U.S.C. 119(e) to U.S. Provisional Application No. 60/917,183 filed on May 10, 2007 and under 35 U.S.C. 119(a) to Patent Application No. PA 2007 00692 filed in Denmark on May 9, 2007, all of which are hereby incorporated by reference into the present application.

TECHNICAL FIELD

This invention relates to novel chromen-2-one derivatives useful as starting material for synthesis of pharmaceuticals.

In other aspects the invention relates to a method of preparing the chromen-2-one derivatives of the invention.

BACKGROUND ART

WO 2006/035034 discloses a group of chromen-2-one derivatives useful as monoamine neurotransmitter re-uptake inhibitors. In this document the (8-H-8-aza-bicyclo[3.2.1]oct-3-yloxy)-chromen-2-one-yl derivatives are synthesized by deprotection of the relevant 8-methyl- or 8-tert-butoxycarbonyl-8-aza-bicyclo[3.2.1]oct-3-yloxy-chromen-2-one derivative.

However, when synthesizing larger amounts of the pharmaceutical compound, the synthesis needs to be scalable, eg. to produce crystalline intermediates and an end product that does not need chromatographic purification.

Further, the process should apply to specific requirements regarding purity and reproducibility.

Therefore, when in connection with the scaling up of this group of compounds a more suitable synthesis was invented.

SUMMARY OF THE INVENTION

In its first aspect, the invention provides a compound of Formula I:

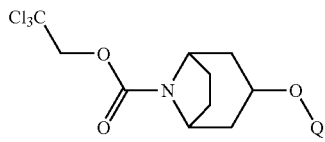

(I)

any of its stereoisomers or any mixture of its stereoisomers, or an addition salt thereof, wherein Q is as defined below.

In its second aspect, the invention provides a method of preparing the compound of Formula I.

Other objects of the invention will be apparent to the person skilled in the art from the following detailed description and examples.

DETAILED DISCLOSURE OF THE INVENTION

Chromen-2-One Derivatives

In its first aspect the present invention provides compounds of Formula I:

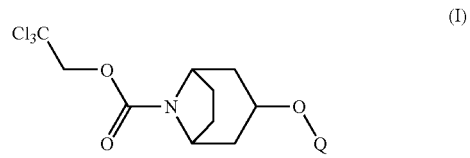

(I)

any of its stereoisomers or any mixture of its stereoisomers, or an addition salt thereof, wherein Q represents chromen-2-one-yl, which chromen-2-one-yl is optionally substituted with one or more substituents independently selected from the group consisting of:

halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

In a further embodiment of the compound of Formula I, Q represents chromen-2-one-yl. In a special embodiment of the compound of Formula I, Q represents chromen-2-one-7-yl. In a further embodiment of the compound of Formula I, Q represents chromen-2-one-6-yl. In a still further embodiment of the compound of Formula I, Q represents chromen-2-one-4-yl.

In a still further embodiment of the compound of Formula I, Q represents substituted chromen-2-one-yl. In a further embodiment, the chromen-2-one-yl group is substituted with a substituent selected from the group consisting of: halo, cyano and alkyl. In a special embodiment of the compound of Formula I, Q represents substituted chromen-2-one-7-yl, such as halo, cyano or alkyl substituted chromen-2-one-7-yl. In a further embodiment of the compound of Formula I, Q represents substituted chromen-2-one-6-yl, such as halo, cyano or alkyl substituted chromen-2-one-6-yl. In a still further embodiment of the compound of Formula I, Q represents substituted chromen-2-one-4-yl, such as halo, cyano or alkyl substituted chromen-2-one-4-yl.

In a further embodiment, Q represents chromen-2-one-yl, which chromen-2-one-yl group is substituted in the 3-position with a substituent selected from the group consisting of: halo, trifluoromethyl, trifluoromethoxy, cyano, hydroxy, amino, nitro, alkoxy, cycloalkoxy, alkyl, cycloalkyl, cycloalkylalkyl, alkenyl and alkynyl. In a special embodiment, the chromen-2-one-yl is substituted in the 3-position with a substituent selected from the group consisting of: halo, cyano and alkyl.

In a still further special embodiment, Q represents 3-halo-chromen-2-one-yl, such as 3-halo-chromen-2-one-6-yl or 3-halo-chromen-2-one-7-yl. In a special embodiment, Q represents 3-bromo-chromen-2-one-6-yl, 3-bromo-chromen-2-one-7-yl, 3-chloro-chromen-2-one-6-yl or 3-chloro-chromen-2-one-7-yl.

In a further special embodiment, Q represents 3-cyano-chromen-2-one-yl, such as 3-cyano-chromen-2-one-6-yl or 3-cyano-chromen-2-one-7-yl.

In a still further embodiment, Q represents chromen-2-one-yl, which chromen-2-one-yl is substituted in the 4-position with a substituent selected from the group consisting of: halo, trifluoromethyl, trifluoromethoxy, cyano, hydroxy, amino, nitro, alkoxy, cycloalkoxy, alkyl, cycloalkyl, cycloalkylalkyl, alkenyl and alkynyl. In a special embodiment, the chromen-2-one-yl is substituted in the 4-position with a substituent selected from the group consisting of: halo, cyano and alkyl. In a further embodiment, Q represents 4-alkyl-chromen-2-one-yl, such as 4-methyl-chromen-2-one-yl, such as 4-methyl-chromen-2-one-6-yl.

In a further embodiment, Q represents chromen-2-one-yl, which chromen-2-one-yl is substituted in the 3- and 4-positions with substituents independently selected from the group consisting of: halo, trifluoromethyl, trifluoromethoxy, cyano, hydroxy, amino, nitro, alkoxy, cycloalkoxy, alkyl, cycloalkyl, cycloalkylalkyl, alkenyl and alkynyl. In a special embodiment, the chromen-2-one-yl is substituted in the 3- and 4-positions with substituents independently selected from the group consisting of: halo, cyano and alkyl. In a further special embodiment, Q represents alkyl-cyano-chromen-2-one-yl, such as methyl-cyano-chromen-2-one-yl, such as 4-methyl-3-cyano-chromen-2-one-yl. In a special embodiment, Q represents 4-methyl-3-cyano-chromen-2-one-6-yl or 4-methyl-3-cyano-chromen-2-one-7-yl.

In a still further embodiment, Q represents an optionally substituted chromen-2-one-4-yl group.

In a further embodiment, Q represents an optionally substituted chromen-2-one-6-yl group.

In a still further embodiment, Q represents an optionally substituted chromen-2-one-7-yl group.

In a special embodiment the chemical compound of the invention is exo-3-(2-oxo-2H-chromen-7-yloxy)-8-aza-bicyclo[3.2.1]octane-8-carboxylic acid 2,2,2-trichloro-ethyl ester, or an addition salt thereof.

Methods of Preparation

In its second aspect the present invention provides a process for preparing a compound of Formula I

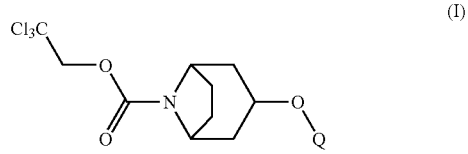

(I)

any of its stereoisomers or any mixture of its stereoisomers, wherein Q represents chromen-2-one-yl,
  which chromen-2-one-yl is optionally substituted with one or more substituents independently selected from the group consisting of:
    halo, trifluoromethyl, trifluoromethoxy, cyano, hydroxy, amino, nitro, alkoxy, cycloalkoxy, alkyl, cycloalkyl, cycloalkylalkyl, alkenyl and alkynyl;
which process comprises:
reacting a 3-hydroxy-8-aza-bicyclo[3.2.1]octane-8-carboxylic acid ethyl ester
with a hydroxy-chromen-2-one,
  which hydroxy-chromen-2-one is optionally further substituted with one or more substituents independently selected from the group consisting of:
    halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

In its third aspect the present invention provides a process for preparing a compound of Formula II

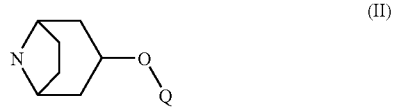

(II)

any of its stereoisomers or any mixture of its stereoisomers, wherein Q represents chromen-2-one-yl,
  which chromen-2-one-yl is optionally substituted with one or more substituents independently selected from the group consisting of:
    halo, trifluoromethyl, trifluoromethoxy, cyano, hydroxy, amino, nitro, alkoxy, cycloalkoxy, alkyl, cycloalkyl, cycloalkylalkyl, alkenyl and alkynyl;
which process comprises:
reacting a compound of Formula I with acid in the presence of a transition metal catalyst

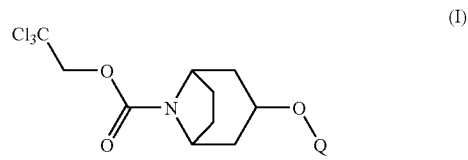

(I)

wherein Q is as defined in formula II.

In one embodiment, the transition metal catalyst is zinc.

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains of from one to six carbon atoms ($C_{1-5}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-hexynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy is O-alkyl, wherein alkyl is as defined above.

Cycloalkoxy means O-cycloalkyl, wherein cycloalkyl is as defined above.

Cycloalkylalkyl means cycloalkyl as above and alkyl as above, meaning for example, cyclopropylmethyl.

Amino is $NH_2$ or NH-alkyl or N-(alkyl)$_2$, wherein alkyl is as defined above.

Addition Salts

The chemical compound of the invention may be provided in any form suitable as a starting material for further synthesis. Suitable forms include addition salts.

Examples of addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be also useful.

In the context of this invention the "onium salts" of N-containing compounds are also contemplated as acceptable addition salts. Preferred "onium salts" include the alkyl-onium salts, the cycloalkyl-onium salts, and the cycloalkylalkyl-onium salts.

Steric Isomers

It will be appreciated by those skilled in the art that the compounds of the present invention may exist in different stereoisomeric forms—including enantiomers, diastereomers or cis-trans-isomers.

For example, the group —O-Q of Formula I may in particular be in the exo or endo configuration relative to the azabicyclic ring.

The invention includes all such isomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2H$ (deuterium), $^3H$ (tritium), $^{13}C$, $^{14}C$, $^{131}I$, $^{125}I$, $^{123}I$, and $^{18}F$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

EXAMPLES

The invention is further illustrated with reference to the following examples, which are not intended to be in any way limiting to the scope of the invention as claimed.

Preparatory Examples

All reactions involving air sensitive reagents or intermediates were performed under nitrogen and in anhydrous solvents. Magnesium sulphate was used as drying agent in the workup-procedures and solvents were evaporated under reduced pressure.

Example 1 endo-3-Hydroxy-8-aza-bicyclo[3.2.1]octane-8-carboxylic acid 2,2,2-trichloro-ethyl ester A mixture of endo-8-methyl-8-aza-bicyclo[3.2.1]octan-3-ol (Tropine) (140 g, 991 mmol) and toluene (2 L) was refluxed using a Dean and Stark apparatus in order to obtain dryness by removing water. 2,2,2-Trichloroethylchloroformate (420 g, 1983 mmol) was added to the mixture during 10-15 minutes, using mechanical stirring. The temperature raises to 35° C. followed by precipitation. The mixture was allowed to stir mechanically for 4 days. The mixture had turned into a thick porridge. Water (500 ml) was added followed by mechanical stirring for 10 min followed by filtration. The crystalline product was washed with petroleum ether (200 ml) and with water (200 ml). Yield 173 g (58%). The filtrate was separated and the organic phase was washed with water (200 ml) and evaporated to about 1 L, The organic phase was put in the refrigerator for 15 h followed by filtration. The crystalline product was washed with petroleum ether (50 ml) and with water (50 ml). Yield 75.6 g (25%). The filtrate was evaporated to half the volume, petroleum ether (250 ml) was added, the mixture was stored in the refrigerator for 15 h followed by filtration. The crystalline product was washed with petroleum ether (20 ml) and with water (20 ml). Yield 10.6 g (4%). The filtrate was stirred with aqueous sodium hydroxide (50 ml, 4 M), phases were separated, the organic phase was washed with water, followed by evaporation. Petroleum ether (200 ml) was added to the mixture and it was allowed to stand in the refrigerator for 15 h followed by filtration. The crystalline product was washed with petroleum ether (20 ml) and with water (20 ml). Yield 3.2 g (1%). Total yield 262.4 g (87%).

Example 2

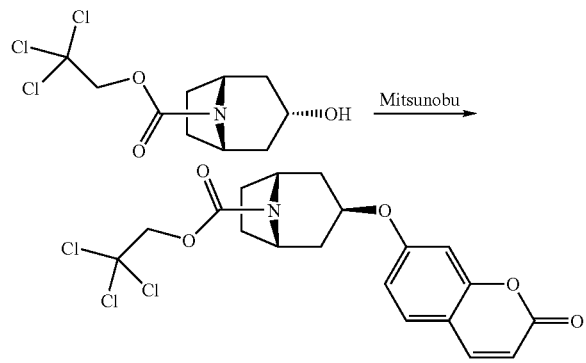

exo-3-(2-Oxo-2H-chromen-7-yloxy)-8-aza-bicyclo [3.2.1]octane-8-carboxylic acid 2,2,2-trichloro-ethyl ester Triphenylphosphine (269.4 g 1027 mmol) was solved in dioxane (1 L). Diethylazodicarboxylate 40% in toluene (450 ml, 1027 mmol) was added to the mixture under ice cooling during 1 h, below 20° C. endo-3-Hydroxy-8-aza-bicyclo [3.2.1]octane-8-carboxylic acid 2,2,2-trichloro-ethyl ester (259 g, 856 mmol) was added during 5 min. No temperature change occurred. The mixture was allowed to stir for 30 min. 7-Hydroxycoumarine (153 g, 942 mmol) was added in portions during 10 min. The temperature rose to 42° C. and the mixture was allowed to stir at room-temperature for 15 h. The reaction-mixture turned into porridge. Aqueous sodium hydroxide (1 L, 4 M) was added and was then stirred for 15 min. The mixture was filtered and the crystals were washed with water (500 ml) and absolute ethanol (2×200 ml). Yield 194.9 (51%).

Example 3

This example illustrates the use of the compound of the invention for synthesizing pharmaceutical compounds.

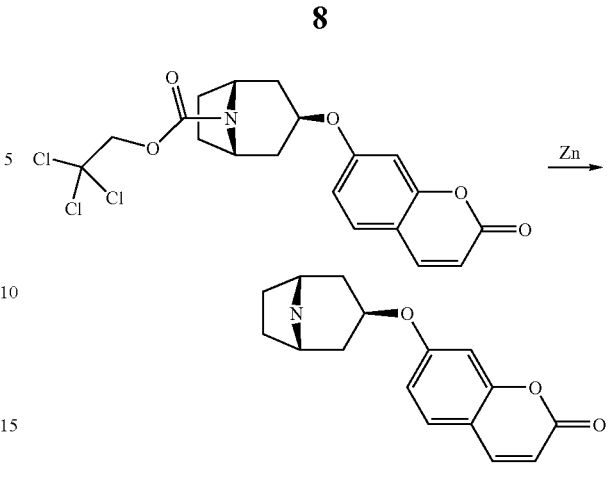

7-[(3-exo)-8-Aza-bicyclo[3.2.1]oct-3-yloxy]- chromen-2-one hydrochloric acid salt exo-3-(2-Oxo-2H-chromen-7-yloxy)-8-aza-bicyclo [3.2.1]octane-8-carboxylic acid 2,2,2-trichloro-ethyl ester (190 g, 425 mmol) was solved in THF (1 L). Water (500 ml) and acetic acid (250 ml) was added. Zinc-powder (69.5 g, 1063 mmol) was added during 2 h and the temperature was allowed to rise to maximum 35° C. The reaction mixture was allowed to stir over the weekend. The mixture was turned into porridge. Water (500 ml) and conc. hydrochloric acid (100 ml, 1.2 mmol) was added. The mixture was stirred for 15 min at room-temperature followed by stirring and ice-cooling for 1 h. The mixture was filtered and the product was washed with cold water (2×200 ml). The crystals were re-crystallized from water (4 L), including warm-filtration: separating the impurity exo-3-(2-oxo-2H-chromen-7-yloxy)-8-aza-bicyclo [3.2.1]octane-8-carboxylic acid 2,2-dichloro-ethyl ester (18 g, 43.7 mmol). The product was allowed to crystallize for 15 h. The crystals were washed with water (2×100 ml), ethanol (3×50 ml) and diethylether (2×150 ml). Yield 73.6 (56%). The mother-liquor was made alkaline by adding aqueous ammonia, followed by filtration. Free base was isolated: yield 21.3 (19%). Total yield of last step 75%.

The invention claimed is:

1. A compound of Formula I:

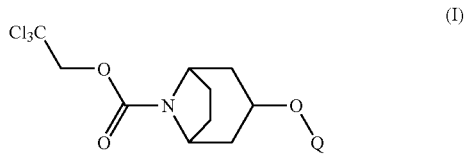

any of its stereoisomers or any mixture of its stereoisomers, or an addition salt thereof,
wherein
Q represents chromen-2-one-yl,
  which chromen-2-one-yl is optionally substituted with
    one or more substituents independently selected from
    the group consisting of:
    halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

2. The compound of claim 1, any of its stereoisomers or any mixture of its stereoisomers, or an addition salt thereof, wherein Q represents chromen-2-one-yl.

3. The compound of claim 1, any of its stereoisomers or any mixture of its stereoisomers, or an addition salt thereof, wherein Q represents chromen-2-one-yl,
which chromen-2-one-yl is substituted with a substituent selected from the group consisting of: halo, cyano and alkyl.

4. The compound of claim 1, any of its stereoisomers or any mixture of its stereoisomers, or an addition salt thereof, wherein Q represents chromen-2-one-yl,
which chromen-2-one-yl is substituted in the 3-position with a substituent selected from the group consisting of: halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

5. The compound of claim 1, any of its stereoisomers or any mixture of its stereoisomers, or an addition salt thereof, wherein Q represents chromen-2-one-yl,
which chromen-2-one-yl is substituted in the 3-position with a substituent selected from the group consisting of: halo, cyano and alkyl.

6. The compound of claim 1, any of its stereoisomers or any mixture of its stereoisomers, or an addition salt thereof, wherein Q represents chromen-2-one-yl,
which chromen-2-one-yl is substituted in the 4-position with a substituent selected from the group consisting of: halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

7. The compound of claim 1, any of its stereoisomers or any mixture of its stereoisomers, or an addition salt thereof, wherein Q represents chromen-2-one-yl,
which chromen-2-one-yl is substituted in the 4-position with a substituent selected from the group consisting of: halo, cyano and alkyl.

8. The compound of claim 1, any of its stereoisomers or any mixture of its stereoisomers, or an addition salt thereof, wherein Q represents chromen-2-one-yl,
which chromen-2-one-yl is substituted in the 3- and 4-positions with substituents independently selected from the group consisting of:
halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

9. The compound of claim 1, any of its stereoisomers or any mixture of its stereoisomers, or an addition salt thereof, wherein Q represents chromen-2-one-yl,
which chromen-2-one-yl is substituted in the 3- and 4-positions with substituents independently selected from the group consisting of:
halo, cyano and alkyl.

10. The chemical compound of claim 1, any of its stereoisomers or any mixture of its stereoisomers, or an addition salt thereof, wherein Q represents an optionally substituted chromen-2-one-4-yl group.

11. The chemical compound of claim 1, any of its stereoisomers or any mixture of its stereoisomers, or an addition salt thereof, wherein Q represents an optionally substituted chromen-2-one-6-yl group.

12. The chemical compound of claim 1, any of its stereoisomers or any mixture of its stereoisomers, or an addition salt thereof, wherein Q represents an optionally substituted chromen-2-one-7-yl group.

13. The chemical compound of claim 1, any of its stereoisomers or any mixture of its stereoisomers, or an addition salt thereof, which is exo-3-(2-Oxo-2H-chromen-7-yloxy)-8-aza-bicyclo[3.2.1]octane-8-carboxylic acid 2,2,2-trichloro-ethyl ester,
or a pharmaceutically acceptable salt thereof.

14. A process for preparing a compound of Formula I

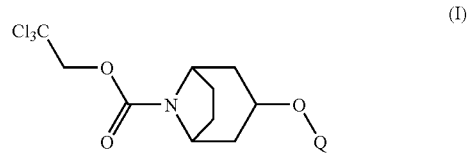

(I)

any of its stereoisomers or any mixture of its stereoisomers, wherein Q represents chromen-2-one-yl,
which chromen-2-one-yl is optionally substituted with one or more substituents independently selected from the group consisting of:
halo, trifluoromethyl, trifluoromethoxy, cyano, hydroxy, amino, nitro, alkoxy, cycloalkoxy, alkyl, cycloalkyl, cycloalkylalkyl, alkenyl and alkynyl;
which process comprises:
reacting a 3-hydroxy-8-aza-bicyclo[3.2.1]octane-8-carboxylic acid ethyl ester
with a hydroxy-chromen-2-one,
which hydroxy-chromen-2-one is optionally further substituted with one or more substituents independently selected from the group consisting of:
halo, trifluoromethyl, trifluoromethoxy, cyano, hydroxy, amino, nitro, alkoxy, cycloalkoxy, alkyl, cycloalkyl, cycloalkylalkyl, alkenyl and alkynyl.

15. A process for preparing a compound of Formula II

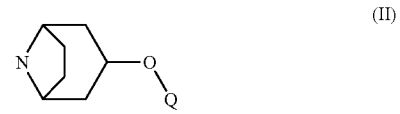

(II)

any of its stereoisomers or any mixture of its stereoisomers, wherein Q represents chromen-2-one-yl,
which chromen-2-one-yl is optionally substituted with one or more substituents independently selected from the group consisting of:
halo, trifluoromethyl, trifluoromethoxy, cyano, hydroxy, amino, nitro, alkoxy, cycloalkoxy, alkyl, cycloalkyl, cycloalkylalkyl, alkenyl and alkynyl;
which process comprises:
reacting a compound of Formula I with acid in the presence of a transition metal catalyst

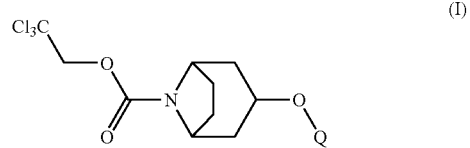

(I)

wherein Q is as defined in formula II.

* * * * *